United States Patent [19]

Abblard et al.

[11] 4,143,059

[45] Mar. 6, 1979

[54] PROCESS FOR PREPARING ALUMINUM ETHYL PHOSPHITE

[75] Inventors: Jean Abblard, Saint Didier Au Mont D'Or; Michel Ghazarian, Décines; René Viricel, Lyon, all of France

[73] Assignee: Philagro S.A., Lyon, France

[21] Appl. No.: 851,794

[22] Filed: Nov. 15, 1977

[30] Foreign Application Priority Data

Nov. 16, 1976 [FR] France .............................. 76 35268
Sep. 7, 1977 [FR] France .............................. 77 27668

[51] Int. Cl.$^2$ ............................................. C07F 5/06
[52] U.S. Cl. ................................................ 260/448 R
[58] Field of Search ..................................... 260/448 R

[56] References Cited

U.S. PATENT DOCUMENTS

| 2,992,262 | 7/1961 | Sears et al. ...................... 260/448 R |
| 3,412,118 | 11/1968 | Kujawa et al. .............. 260/448 R X |
| 3,474,464 | 10/1969 | Matthews et al. ........... 260/448 R X |

OTHER PUBLICATIONS

Arlovski et al., J. Gen. Chem., USSR vol. 42, pp. 1924–1927 (1972).

*Primary Examiner*—Helen M. S. Sneed
*Attorney, Agent, or Firm*—Browdy and Neimark

[57] ABSTRACT

Aluminum ethyl phosphite, useful as a plant fungicide, is made in an industrial process in high yield and good quality by reacting an excess of a ternary mixture of diethyl phosphite, monoethyl phosphite and phosphoric acid, with alumina at 20–200° C. under subatmospheric pressure, while eliminating water formed during the reaction.

15 Claims, No Drawings

PROCESS FOR PREPARING ALUMINUM ETHYL PHOSPHITE

FIELD OF THE INVENTION

The present invention relates to a process for preparing aluminum ethyl phosphite.

BACKGROUND OF THE INVENTION

Aluminum ethyl phosphite is described in U.S. patent application Ser. No. 531,387 filed on Dec. 10, 1974 as the active agent of fungicidal compositions usable to protect plants. Since this product has proved useful, an industrial manufacturing process was sought.

It is known that aluminum ethyl phosphite may be prepared by dealkylating a phosphite dialkyl by means of a salt, particularly an aluminum chloride. (of V.V. Orfovski et. al., Journal of Gen. Chem. USSR Vol. 42 p 1927-1972)

It has also been proposed that aluminum ethyl phosphite be prepared in a two-stage process: first, saponification by an alkaline hydroxide, in particular soda, of diethyl phosphite to obtain sodium ethyl phosphite, which is then subjected to a double exchange reaction in the presence of a water-soluble aluminum salt. (of U.S. patent appln. Ser. No. 531,387)

It is also known that metal salts of phosphorus monoesters with an alkyl chain containing 1 to 4 carbon atoms may be prepared by reaction, in an anhydrous environment and in the absence of solvents, of a metallic hydroxide at a temperature of about 90° to 150° C. with a dialkyl phosphite. In fact, no illustration of this process is given in the case of preparation of aluminum ethyl phosphite. (of German patent appln. No. 2513965)

When the attempt is made to react diethyl phosphite, which for convenience will be called by its abbreviation DIEP in the remainder of the specification, with hydrated alumina, it is found that hydrolysis is carried out in the proper manner only at temperatures about 150° C. and gives rise to a small portion of monoethyl phosphite (MEP) which indubitably plays the role of catalyst so that an aluminum ethyl phosphite with variable appearance and characteristics is obtained. These two properties render the process utterly unusable on an industrial scale.

It is also known that MEP reacts with alumina at a moderate temperature (80° C.). However, this substance (MEP) has never been prepared and used industrially because of its balanced decomposition into DIEP and phosphoric acid.

SUMMARY OF THE INVENTION

It is accordingly an object of the present invention to overcome the deficiencies of the prior art, such as indicated above. It is another object to make aluminum ethyl phosphite without the problems indicated above, and in good yield. It is a further object to provide a process for making aluminum ethyl phosphate in particular, which process can be readily used industrially.

The present invention thus proposes a process for preparing aluminum ethyl phosphite under conditions permitting excellent reproducibility with a very good yield.

The process according to the present invention consists in causing an excess of ternary mixture, in equilibrium, of (in mols):
  23 to 93% diethyl phosphite (DIEP)
  59 to 7% monoethyl phosphite (MEP)
  18 to 0.1% phosphoric acid (PA)
to react with alumina, possibly hydrated alumina, at a temperature between 20° and 100° C. at a reduced pressure, the water evolved from the reaction being eliminated simultaneously with its formation.

DETAILED DESCRIPTION OF EMBODIMENTS

Since MEP is not obtained industrially, one essentially has to employ it in the form of a ternary mixture with DIEP and phosphoric acid (PA). A convenient method consists of allowing or causing a mixture of 55 to 98% (in mols) DIEP and 45 to 2% phosphoric acid to evolve. Equilibrium is progressively established by production of monoethyl phosphite according to the reaction:

$$DIEP + PA \rightleftarrows 2\ MEP.$$

At ambient temperature, the reaction rate is slow so that it is useful to heat the mixture to arrive at equilibrium in a reasonable time. Thus, for example, a ternary mixture as defined above can be obtained by heating a binary mixture of (in mols):
  55 to 98% and preferably 64 to 90% DIEP, and
  45 to 2% and preferably 36 to 10% PA
for 15 minutes to one hour at 150° C.

Also, the addition of a small proportion of triethyl phosphite to the starting mixture is possible although not useful. Under these conditions, triethyl phosphite disappears almost entirely so that once again we have DIEP and/or MEP. Thus its presence is not prejudicial inasfar as regards the equilibrium proportions of DIEP, MEP, and phosphoric acid being within the limits of the invention.

It has also been found that this ternary mixture can be obtained in advance by another process which consists of reacting phosphorus trichloride with an ethanol-water mixture according to the reaction:

$$PCl_3 + aC_2H_5OH + (3-a)H_2O \rightarrow DIEP + MEP + PA + 3HCl$$

"a" being the number of mols of ethanol per mol of $PCl_3$. The proportions in the ternary mixture depend on the transesterification coefficients:

$$R = (OH)/(C_2H_5)(OH)$$

according to the relation (for one mol of $PCl_3$):
  ethanol: 2-2R
  water: 2R + 1.

The reaction is conducted at a low temperature, preferably between 0° and 20° C., to limit the formation of carbonium ions and consequent formation of ethyl chloride. With the same aim in view, and preferably in this order, phosphorus trichloride is poured into the water-alcohol mixture. Finally, and still for the same reasons, it is important to remove the hydrochloric acid formed from the reaction medium as quickly as possible. This elimination can be performed either at low temperature or at a high temperature in a very short time. In practice, the hydrochloric acid is continuously stripped.

Alumina, possibly hydrated alumina, usable in this process may come in various forms. Experience has shown that the hydrargillite ($Al(OH)_3$) form gives the best results. The examples described in the present application illustrate the use of various types of alumina differing from each other by their specific surface (5 to 30m$^2$/g) for hydrargillites, or by the degree of hydration for the hydrated aluminas and gels.

The ternary mixture in equilibrium is placed in contact with the alumina using excess porportions of 50 to 200% in mols with respect to the alumina. In other words, for stoichiometry, one mol of alumina is needed for 3 mols of phosphites (DIEP + MEP + phosphoric acid). Thus, according to the invention the proper number of phosphite mols per mol of alumina is, in this case, between 4.5 and 9 mols.

More specifically, it has been found that the most favorable proportions at equilibrium of the mixture according to the invention are, in mols:

35 to 78% for DIEP,
54 to 20% for MEP,
11 to 1% for phosphoric acid.

Mixtures richer in DIEP and hence poorer in MEP and phosphoric acid give lower yields, since the MEP is no longer sufficient to react completely with the alumina and the temperature is insufficient for the DIEP-alumina reaction to take place at an acceptable rate. On the other hand, mixtues too rich in MEP and phosphoric acid give rise to the formation of mixed salts of alumina, MEP, and phosphoric acid during the reaction, which diminishes the pure aluminum ethyl phosphite yield by that amount. The proportions of the mixture in equilibrium indicated above are chosen such that, for a given mixture, the proportions remain constant during the reaction. Thus, the process can be carried out continuously.

This process is carried out at a moderate temperature, preferably between 20° and 100° C. and advantageously between 40° and 90° C., this temperature range favoring the reaction of MEP with alumina. At the same time, the pressure is reduced and the water driven off by distillation as it is formed, resulting in the following MEP-alumina reaction:

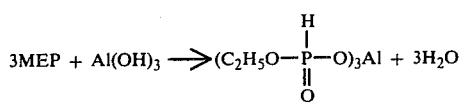

Elimination of the water prevents the water from reacting with the MEP to form excess phosphoric acid, the proportion of which, if it exceeds the equilibrium value, shifts the equilibrium in such a way as to decrease the yield, as explained above. It is thus essential to drive off the water in order to ensure constant reaction conditions, stabilizing the mixture at equilibrium. The value of the low pressure necessary varies according to the conditions, particularly quantities, apparatus volume, etc. It has been observed that reactions at 30 to 180 mm Hg give satisfactory results.

More specifically, the process can be operated as follows:

A mixture of DIEP and phosphoric acid is heated to a relatively high temperature until equilibrium is reached. The mixture at equilibrium of DIEP, phosphoric acid, and MEP is then, in turn, mixed with the alumina and raised to the reaction temperaure (80° to 90° C.). The reaction is very fast.

However, since it corresponds to the action of MEP and some DIEP remains, this reaction is not a total one. Moreover, the water is not completely driven off because of the rapidity of its formation. As a result, according to a particular embodiment of the invention, the reaction described above is followed, continuously, by a second finishing stage: reaction of DIEP with water at a high temperature (for example 150° C.) at atmospheric pressure to produce supplementary MEP which, in its turn, reacts with the remaining alumina. Under these conditions the ethanol formed during the reaction is eliminated by distillation. This operation is longer than the former operation and may take 20 minutes to one hour. The reaction mixture is cooled to ambient temperature; then the aluminum ethyl phosphite is isolated and purified in the usual way (washing, filtration, and drying). The mother liquors containing the unreacted phosphites are recycled and, possibly after distillation of the ethanol used for washing, a fresh mixture of phosphites is added to them in the same proportions as the mixture at equilibrium, as well as the quantity of alumina necessary for a new operation. This recycling is possible due to the constancy of the relative proportions of DIEP, MEP, and phosphoric acid during the reaction.

This process gives a very good yield, greater than 90% and often almost quantitative. Moreover, the quality of the aluminum ethyl phosphite obtained is excellent.

When it is desired to use this process in large units for continuous production of large quantities of aluminum ethyl phosphite, it is preferable to operate at lower temperatures than the temperatures of 80° to 90° C. indicated above. The heating time necessary to bring the initial mixture to a relatively high temperature in reactors with capacities of several hundred or even thousand liters is long. Moreover, distillation of the water formed by the reaction lasts longer. This being the case, there is a delay between formation of the water and its removal. The water is thus in prolonged contact with the DIEP and the MEP at a relatively high temperature, which causes substantial hydrolysis of these two compounds. As a result the mixture is enriched with MEP and PA such that the constancy conditions are no longer adhered to and the recycling capacity of the process is limited as a consequence.

In this case, it is advantageous to operate at temperatures between about 40° and 70° C., which are more favorable to the MEP-alumina reaction, from a ternary mixture of, in mols:

35 to 78% DIEP
54 to 20% MEP
11 to 1% phosphoric acid.

The best results are obtained when the quantity of MEP in this mixture is stoichiometric with alumina, namely the MEP/alumina molar ratio is 3:1. Aside from these more particular conditions, the method of operation is the same as described above.

Hence, the point of this embodiment is that the temperature is more moderate and hence more economical, and it is easier to recycle and obtain a purer product, which is important because the product is to be applied as a plant fungicide.

The following examples are given as nonlimitative examples to illustrate the process of the present invention:

EXAMPLES 1 to 15

In a prior operation, 6.3 mols (751 g) of a mixture of:
70% diethyl phosphite
30% phosphoric acid
in a molar percentage is heated for 3 minutes at 150° C. and there is thus obtained the same weight of a ternary mixture of:
43% diethyl phosphite 49% monoethyl phosphite
8% phosphoric acid
in the mols.

Alumina (78 g, 1 mol) of the $H_{10}$ type, namely a hydrargillite, with a specific surface of 10 $m^2/g$, is then added.

The reactor is then set at a low pressure (40 mm Hg) and the mixture is vigorously stirred. The reaction medium, initially at 25° C., heats progressively, reaching 50° C. in 50 minutes. It is then heated slightly and the water formed is distilled off in 15 to 20 minutes. During distillation, the temperature of the medium rises to 50° C. and reaction is allowed to continue for 15 extra minutes at this temperature.

The entire reaction lasts one hour, 30 minutes. Ethanol (100 g) is then added and the mixture is cooled to ambient temperature. The aluminum ethyl phosphite precipitates, is spun-dried, then rinsed with absolute ethyl alcohol. In this way, aluminum ethyl phosphite is obtained with a yield of 84.2% of a compound with a purity titration of 95.2% with respect to the alumina.

The mother liquors are replaced in the reactor and the alcohol is distilled. 78 g (1 mol) of the same alumina as before are added to the mother liquors (427 g) in the reactor. Finally, 333 g (4.9 M) of fresh DIEP/MEP/PA mixture are added so that there are 6.3 M of phosphites as at the beginning of the preceding cycle.

The operation is repeated 14 times under the same conditions. For each recycling, the various parameters are measured, in particular titer and yield.

Under these conditions it is observed that:
the proportions of diethyl phosphite/monoethyl phosphite and phosphoric acid in the phosphite mixture remain essentially constant with a slight shift toward MEP;
the recycling yields vary from 89 to 100% with a general means of 96% and the aluminum titers from 94 to 98% with a general mean of 97%. (relative to the theoretical content)

EXAMPLES 16 to 18

These are conducted in the manner of the preceding examples, non-hydrated alumina being replaced successively by other grades of alumina, namely:

a similar alumina (hydrargillite), but with a specific surface equal to about 20 $m^2/g$: under these conditions the exothermicity increases more rapidly (30 min.), the reaction is faster (1 hour) and the yields obtained are very good (95%), which shows a greater reactivity of this alumina than that of the preceding examples.

an alumina, SH 100 LEA, hydrated to 15.2% and made by Rhone-Poulenc Industries: under these conditions it is necessary to heat the reaction medium from the very beginning to start the reaction. The yields are also very good (95%).

an amorphous gel, type LEA, 19% water, manufactured by Rhone-Poulenc Industries: this alumina is highly reaction because the exothermicity develops in 10 minutes and the reaction lasts only half an hour. The yields are about 90%.

EXAMPLE 19

Results similar to those of Examples 1 to 15 are obtained when the ternary mixture is prepared by pouring phosphorous trichloride (3 mols) for 2 and a half hours on 4.20 mols 94% ethanol and 4.8 mols distilled water. During the first half of the pouring, the reaction is maintained at less than 15° C. with a cooling bath. Then hydrochloric acid begins to evolve (for 15 minutes), and the cooling is removed, the temperature of the reaction medium being 6° C.

At the end of pouring, the hydrochloric acid is drawn off by allowing the reaction to proceed at low pressure (25 to 30 mm Hg) which operation is complete in 2 hours.

EXAMPLES 20 to 80

In a prior operation 1.5 mol (193 g) of a mixture of:
85% diethyl phosphite,
15% phosphoric acid
in a molar percentage is heated for 30 minutes at 150° C.
At the end of the reaction a mixture in equilibrium of:

| 67.5% diethyl phosphite | |
| 29.7% monoethyl phosphite | phosphites |
| 2.7% phosphoric acid | | is obtained.

This mixture is placed in a 500 ml reactor together with 0.2 mol (15.6 g) of $Al(HO)_3$ hydrated alumina of the H10 hydrargillite type. The quantitites chosen correspond to 150% excess phosphites (stoichiometry being 0.6 mol phosphites). The volume of the mixture is about 20 ml.

The reactor charged in this way is set to a low pressure (P=130 mm Hg), then heated to 80° C. under agitation. As soon as this temperature is reached, the reaction begins and the water formed is distilled (in a Vigreux column). The temperature rises gradually to 100° C. When this temperature, is reached, the vacuum is broken and the reactor returns to atmospheric pressure (t= 150° C.). This end of the operation favors regeneration of monoethyl phosphite from the diethyl phosphite and residual water. The operation lasts a total of 7 minutes.

The reactor is then heated to drive the steam to the top of the column. When the temperature at the head of the column goes down to 84° C. (which requires about 10 minutes), the ethanol formed is distilled, which causes the temperature at the foot of the column to rise. When this reaches 150° C. (which takes 10 minutes), distillation is stopped. Heating at 150° C. is continued for 5 minutes to optimize the yield by favoring the diethyl-phosphite/alumina reaction.

The reaction mixture is then cooled to ambient temperature; then 30 g ethanol are added. The alumina ethyl phosphite is spun-dried, then rinsed with absolute ethanol which is added to the mother liquors.

These liquors, which contain unreacted phosphites and the rinsing alcohol, are recycled in the reaction and the alcohol is distilled under the foot temperature is 150° C.

The remaining phosphite mixture is completed to 1.5 mol by addition of a mixture of DIEP, MEP, and phosphoric acid, then 0.2 mol $H_{10}$ hydrargillite is added and the set of operations can be recommenced. The latter phase lasts 30 to 45 minutes.

Recycling is done 59 times. Each time the various parameters and yields of the reaction are measured.

Under these conditions it is observed that:
the proportions of DIEP, MEP, and phosphoric acid in the "phosphite" mixture remain essentially constant;

the gross yields vary from 92.2 to 98.8% and the aluminum titers from 97 to 100%, while the recycled yield varies from 90 to 100%.

This shows clearly that due to the constancy of the mixture at equilibrium the process lends itself to numerous recycling operations and, in any event, the yields are excellent and often practically quantitative.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A process for manufacturing aluminum ethyl phosphite which comprises reacting an excess of a ternary mixture in equilibrium of, in mols:
   23 to 93% diethyl phosphite,
   59 to 7% monoethyl phosphite,
   18 to 0.1% phosphoric acid
with alumina at a temperature between 20° and 100° C., at subatmospheric pressure, the water resulting from the reaction being simultaneously eliminated as it is formed.

2. A process according to claim 1, wherein the starting ternary mixture comprises, in mols:
   35 to 78% diethyl phosphite,
   54 to 20% monoethyl phosphite,
   11 to 1% phosphoric acid.

3. A process according to claim 1, wherein the alumina is a hydrargillite.

4. A process according to claim 1, wherein said alumina is in the hydrated or gel form.

5. A process according to claim 1, wherein the ternary mixture is present in a 50 to 200% (in mols) excess with respect to stoichiometry.

6. A process according to claim 5, wherein said ternary mixture comprises:
   35 to 78% diethyl phosphite,
   54 to 20% monoethyl phosphite,
   11 to 1% phosphoric acid.

7. A process according to claim 1, wherein the temperature during said reaction is between 40° and 70° C.

8. A process according to claim 1, wherein when the temperature reaches 100° C., the reactor is reset to atmospheric pressure, and heated to 150° C., then kept at this latter temperature for a few minutes to complete the reaction.

9. A process according to claim 1, further comprising, after said reaction, cooling the mixture to ambient temperature, recovering precipitated aluminum ethyl phosphite, and spin-drying and washing said precipitate.

10. A process according to claim 1, further comprising, after said reaction, recovering aluminum ethyl phosphite and mother liquor, cooling and recycling the mother liquor, topping up the phosphite mixture in the mother liquor to the starting molar quantity, adding a stoichiometric quantity of alumina and repeating the reaction.

11. A process according to claim 1, wherein the ternary mixture is prepared from a mixture of (in mols)
   55 to 98% diethyl phosphite, and
   45 to 2% phosphoric acid,
which is heated to 150° C. for 15 minutes to 1 hour.

12. A process according to claim 11, wherein the starting mixture comprises (in mols):
   64 to 90% diethyl phosphite, and
   36 to 10% phosphoric acid.

13. A process according to claim 1, wherein the ternary mixture is prepared by the action of phosphorus trichloride on an ethanol-water mixture according to the reaction:

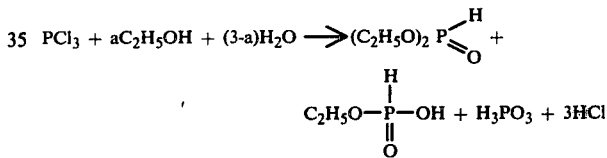

14. A process according to claim 13, wherein said phosphorus trichloride is poured on said ethanol-water mixture at a temperature between 0° and 20° C. and the hydrochloric acid is eliminated as it is formed.

15. A process according to claim 3, wherein the hydrargillite has a specific surface of 5 to 30 m²/g.

UNITED STATES PATENT AND TRADEMARK OFFICE
CERTIFICATE OF CORRECTION

PATENT NO. : 4,143,059
DATED : March 6, 1979
INVENTOR(S) : Jean Abblard et al.

It is certified that error appears in the above-identified patent and that said Letters Patent are hereby corrected as shown below:

In the title page, Other Publications, "Arlovski" should read --Orlovski--

In the Abstract, line 5, "200°" should read --100°--

Column 1, line 18, "Orfovski" should read --Orlovski--
        line 19, "1927-1972)" should read --1927 (1972).--

Column 2, line 47, the formula should read:

$$ R = \frac{(OH)}{(C_2H_5)+(OH)} $$

Column 3, line 22, "mixtues" should read --mixtures--

Column 5, line 12, "50°" should read --60°--
        line 39, "theontical" should read --theoretical--

Signed and Sealed this

Twenty-sixth Day of February 1980

[SEAL]

*Attest:*

SIDNEY A. DIAMOND

*Attesting Officer*     *Commissioner of Patents and Trademarks*

UNITED STATES PATENT AND TRADEMARK OFFICE
CERTIFICATE OF CORRECTION

PATENT NO. : 4,143,059
DATED : March 6, 1979
INVENTOR(S) : Jean ABBLARD et al.

It is certified that error appears in the above-identified patent and that said Letters Patent are hereby corrected as shown below:

Abstract, line 4, "phosphoric" should read --phosphorous--
Column 1, line 50, "phosphoric" should read --phosphorous--
Column 2, lines 1, 10, 12 and 33, "phosphoric" should read --phosphorous--
Column 3, lines 7, 18, 24, 44, 56 and 58-59, "phosphoric" should read --phosphorous--
Column 4, lines 17, 46, and 64, "phosphoric" should read --phosphorous--
Column 5, lines 2 and 33, "phosphoric" should read --phosphorous--
Column 6, line 13, "phosphoric" should read --phosphorous--
Column 6, line 67, "phosphoric" should read --phosphorous--
Column 7, lines 26, 35 and 47, "phosphoric" should read --phosphorous--
Column 8, lines 23 and 28, "phosphoric" should read --phosphorous Signed and Sealed this Fifteenth Day of July 1980

[SEAL]

Attest:

SIDNEY A. DIAMOND

Attesting Officer     Commissioner of Patents and Trademarks